United States Patent
Loyen

(10) Patent No.: US 10,463,889 B2
(45) Date of Patent: Nov. 5, 2019

(54) COSMETIC COMPOSITION COMPRISING A FINE POWDER

(75) Inventor: Karine Loyen, Pont-Audemer (FR)

(73) Assignee: Arkema France, Colombes (FR)

( * ) Notice: Subject to any disclaimer, the term of this patent is extended or adjusted under 35 U.S.C. 154(b) by 1196 days.

(21) Appl. No.: 12/595,672

(22) PCT Filed: Apr. 14, 2008

(86) PCT No.: PCT/FR2008/050662
§ 371 (c)(1),
(2), (4) Date: Feb. 23, 2010

(87) PCT Pub. No.: WO2008/145889
PCT Pub. Date: Dec. 4, 2008

(65) Prior Publication Data
US 2010/0215701 A1    Aug. 26, 2010

(30) Foreign Application Priority Data
Apr. 12, 2007 (FR) .................... 07 54431

(51) Int. Cl.
*A61Q 19/00* (2006.01)
*A61K 8/88* (2006.01)

(52) U.S. Cl.
CPC ............. *A61Q 19/00* (2013.01); *A61K 8/88* (2013.01)

(58) Field of Classification Search
None
See application file for complete search history.

(56) References Cited

U.S. PATENT DOCUMENTS

| 4,438,095 A | 3/1984 | Grollier et al. |
| 4,610,919 A | 9/1986 | Kent |
| 2002/0082382 A1 | 6/2002 | Le Crom et al. |
| 2006/0115504 A1* | 6/2006 | Loyen et al. ............ 424/401 |
| 2008/0167418 A1 | 7/2008 | Kong et al. |

FOREIGN PATENT DOCUMENTS

| DE | 10 2004 058 073 A1 | 6/2006 |
| EP | 1 172 396 A1 | 1/2002 |
| FR | 2 478 465 A1 | 9/1981 |
| JP | 2007-56085 A | 3/2007 |
| WO | WO 2006/126563 A1 | 11/2006 |
| WO | WO 2008/006782 A1 | 1/2008 |

OTHER PUBLICATIONS

International Search Report of PCT/FR2008/050662 (dated Nov. 28, 2008).
Y. Nakajima et al., "Polyamide Resin Fine Particles Useful for Cosmetics and Process for Production Thereof", XP002461756—Database [Online] Chemical Abstracts Service—Database Accession No. 2006:1252602.
Database WPI Week Aug. 2007—Thomson Scientific 2007-083526—XP002461757.

\* cited by examiner

*Primary Examiner* — Nannette Holloman
(74) *Attorney, Agent, or Firm* — Millen, White, Zelano and Branigan, P.C.

(57) ABSTRACT

The present invention relates to cosmetic compositions used in the care and make-up field. This composition mainly comprising a continuous aqueous phase, a fatty phase and a fine and porous pulverulent copolyamide powder phase, is in the form of creamy, liquid or gelled compositions. This is in particular an emulsion, but it may also be a two-phase formulation or composition in which the fatty phase and aqueous phase are separate. The invention more particularly relates to cosmetic care and/or make-up compositions having a continuous aqueous phase in the case of an oil-in-water emulsion.

11 Claims, No Drawings

COSMETIC COMPOSITION COMPRISING A FINE POWDER

The present invention relates to cosmetic compositions used in the care and make-up field. This composition mainly comprising a continuous aqueous phase, a fatty phase and a fine and porous pulverulent copolyamide powder phase, is in the form of creamy, liquid or gelled compositions. This is in particular an emulsion, but it may also be a two-phase formulation or composition in which the fatty phase and aqueous phase are separate. The invention more particularly relates to cosmetic care and/or make-up compositions having a continuous aqueous phase in the case of an oil-in-water emulsion.

The use of surfactants, thickeners and more generally of surface-active agents in the emulsion type cosmetic compositions according to the invention makes it possible to obtain a stable dispersion of one phase in the other. It is also possible to have, in the compositions according to the invention, additives such as preservatives and fragrances, but also cosmetic active agents such as moisturizers (polyols), UV screening agents, antiwrinkle agents, self-tanning agents, film-forming agents, antioxidants and many others.

Another subject of the invention is a process for making up and/or caring for keratinous substances such as the skin, lips, nails, hair, eyelashes, eyebrows or body hair of humans, comprising the application of the composition according to the invention onto the keratinous substances.

The composition according to the invention may be a composition for making up and/or caring for keratinous substances, in particular a face care composition (such as, for example, a cream or fluid having a moisturizing, anti-wrinkle and/or make-up removing, etc. property and also a moisturizing and/or makeup-removing two-phase lotion), a body care composition (such as a moisturizing or slimming composition), a waterproof or non-waterproof sun cream composition, a skin makeup composition, such as a foundation, an eye shadow, a mascara, a blusher, a concealer or a body makeup product.

Compositions of continuous aqueous phase type have many advantages from the cosmetic and galenic viewpoint. They are especially low-cost and comfortable to use as they do not have a greasy feel. However, their drawback is that they have a consistency that is too close to the consistency of water to be attractive for consumers and they have application difficulties. In addition, after the feeling of moisture on the skin has disappeared, they improve neither the comfort, nor the care, nor the visual appearance of the skin (for example, no powdered appearance).

These problems may be solved by adding thickeners or polyols which will give consistency to the formulations. However, this type of product often makes the formulations difficult to apply because of a tacky, even sticky effect due to the presence of polyols. Furthermore, these additives leave a shiny effect on the skin after application and may have occlusive effects at the pores of the skin.

In document EP 1582194, a cosmetic composition is described comprising a liquid, cream or powder base, a fragrance and a powder formed from spherical, cylindrical or dumbbell-shaped polyamide (abbreviated to PA) particles. These particles are porous, have an average diameter of 1 to 30 µm, a specific surface area of 5 m²/g or more, a linseed oil absorption of 200 ml/100 g or more, a crystallinity of 40% or higher and a ratio of the volume-average diameter relative to the number-average diameter of 1.0 to 1.5. The homopolyamide PA-12 or PA-6 powder of these compositions causes a light-scattering effect at the surface of the skin and has a high sebum absorptivity, which effectively diminishes abnormal light reflection produced on the skin at the time when said compositions are applied to the skin.

Furthermore, in said document EP1582194, an example shows that the homopolyamide PA-6 powders, manufactured as described in the text, give sensory properties of the type that give a feeling of richness when they are applied, that are greater than those of homopolyamide PA-12 powders, when they are introduced into a foundation.

However, it has been observed, after research work, that the polyamide powders described in this prior art, do not make it possible to solve the problems encountered for compositions having a continuous aqueous phase: indeed the homopolyamide PA-6 powders, although they greatly increase the consistency of formulations having a continuous aqueous phase, giving the user the feeling of richness that is expected at the time of application, they do not result, after application of the formulation, in a soft feel.

Conversely, the homopolyamide PA-12 powders have practically no effect on the consistency of formulations having a continuous aqueous phase. These retain, despite the addition of polyamide powder, the consistency of water that is not very much appreciated by the users. On the other hand, the feel left on the skin after application is very soft.

It has now been discovered that by using copolyamide powders, it is possible to prepare compositions having continuous aqueous phases that give a feeling of richness to said composition, expected by the users, and leave, after application, a soft powdered feel.

One subject of the invention is a composition that comprises (i) an aqueous phase, (ii) a fatty phase and (iii) a pulverulent phase comprising a copolyamide powder derived from the polymerization of at least two different monomers described below and optionally of other compounds defined below. This composition may be an emulsion having a continuous aqueous phase (oil-in-water) or a two-phase composition having a separate aqueous phase and fatty phase.

The continuous aqueous phase, according to the invention, may comprise thickeners, emollients, humectants (such as polyols) and/or moisturizers.

The fatty phase, according to the invention, may comprise solid or liquid fatty substances of plant, mineral, animal or synthetic origin. Mention may be made, for example, of esters, fatty alcohols, fatty acids, hydrocarbons comprising essentially carbon and hydrogen atoms and optionally nitrogen or oxygen atoms. Mention may also be made of silicone oils and fluorinated oils.

According to one embodiment, the composition is characterized in that the powder particles have an average diameter ranging from 1 µm to 200 µm, preferably from 1 to 100 µm, even more preferentially from 1 to 50 µm, even more advantageously from 1 to 20 µm, a specific surface area between 1 and 25 m²/g and a spheroidal shape.

According to one embodiment, the composition is characterized in that it comprises (% by weight relative to the total composition):
 59.9 to 98.9%, preferably 69 to 95%, of aqueous phase;
 0.1 to 30%, preferably 1 to 20%, of pulverulent coPA powder phase; and
 40 to 1% of a fatty phase.

According to one embodiment, the composition is characterized in that the aqueous phase comprises from 1 to 99% (% by weight relative to the total composition) of polyols, preferably 10 to 60%.

According to one embodiment, the composition is characterized in that it comprises at least one cosmetic ingredient chosen from antioxidants, fragrances, preservatives, neutralizing agents, surfactants, film-forming polymers, thickeners, ultraviolet screening agents, vitamins, colouring materials, emulsion stabilizers, moisturizers, self-tanning compounds, antiwrinkle active agents and mixtures thereof.

According to one embodiment, the composition is characterized in that this is a moisturizing, antiwrinkle and/or make-up-removing face care cream or fluid, a moisturizing and/or slimming body care cream or fluid, a waterproof or non-waterproof sunscreen, a foundation, an eye shadow, a mascara, a blusher, a concealer or a body makeup product, a two-phase moisturizing or make-up-removing lotion.

The invention also relates to the use of a composition for manufacturing a make-up and/or care product for the skin which gives the skin a soft feel and a matte and powdered appearance after application onto said skin.

The invention also relates to a cosmetic process for making up and/or caring for keratinous substances, comprising application to these substances of a composition as described previously.

According to one embodiment, the use of the fine and porous powder is characterized in that the powder particles have an average diameter ranging from 5 to 20 μm.

According to one embodiment, the use of the fine and porous powder is characterized in that the powder particles have a spheroidal shape.

The invention will now be described in further detail.

Powder

Regarding the copolyamide powder (abbreviated to coPA powder) this is understood to mean the condensation products of at least two different monomers chosen from:
  amino acid type monomers;
  lactam type monomers having between 3 to 12 carbon atoms on the main ring and possibly being substituted;
  monomers derived from the reaction between an aliphatic diamine having between 6 and 12 carbon atoms and a dicarboxylic acid having between 4 and 18 carbon atoms; and
  blends thereof, with monomers having a different number of carbon atoms in the case of blends between an amino acid type monomer and a lactam type monomer.

As examples of lactams, mention may be made of those having from 3 to 12 carbon atoms on the main ring and possibly being substituted. Mention may be made, for example, of β,β-dimethylpropriolactam, α,α-dimethylpropriolactam, amylolactam, caprolactam, capryl lactam, oenantholactam, 2-pyrrolidone and lauryl lactam.

As examples of dicarboxylic acids, mention may be made of acids having between 4 and 18 carbon atoms. Mention may be made, for example, of from adipic acid, sebacic acid, azelaic acid, suberic acid, isophthalic acid, butanedioic acid, 1,4-cyclohexyldicarboxylic acid, terephthalic acid, the sodium or lithium salt of sulphoisophthalic acid, dimerized fatty acids, (these dimerized fatty acids have a dimer content of at least 98% and are preferably hydrogenated) and dodecanedioic acid HOOC—$(CH_2)_{10}$—COOH.

As examples of a diamine, it may be an aliphatic diamine having from 6 to 12 carbon atoms, it may be a saturated acrylic and/or cyclic diamine. By way of example, mention may be made of hexamethylenediamine, piperazine, tetramethylenediamine, octamethylenediamine, decamethylenediamine, dodecamethylenediamine, 1,5-diaminohexane, 2,2,4-trimethyl-1,6-diaminohexane, diaminepolyols, isophoronediamine (IPD), methylpentamethylenediamine (MPDM), bis(aminocyclohexyl)methane (BACM), bis(3-methyl-4-aminocyclohexyl)methane (BMACM), methaxylyenediamine, bis(p-aminocyclohexyl)methane and trimethylhexamethylenediamine.

In the case of synthesizing a coPA from lactams by an anionic route, the method consists in suspending the lactam in an organic liquid or dissolving it in a solvent and in carrying out an anionic type polymerization that makes it possible to directly obtain the coPA powder which separates by itself from the liquid medium as it is formed. The method for the anionic polymerization of lactams is essentially based on the use of a catalyst such as sodium or one of its compounds such as sodium hydride or sodium methylate and of an activator such as N-carboxyanilide lactams, isocyanates, carbodiimides, cyanimides, acyl lactams, triazines, ureas, N-substituted imides, and esters, amongst others, optionally in the presence of a finely divided mineral or organic filler having the role of a crystallization seed, such as PA powder (for example, ORGASOL® powder), silica powder, or talc powder and in the presence of an N,N'-alkylenebisamide, more particularly, N,N'-ethylenebisstearamide, N,N'-ethylenebisoleamide, N,N'-ethylenebispalmitamide, N,N'-ethylenebisgadoleamide, N,N'-ethylenebiscetoleamide and N,N'-ethylenebiserucamide, N,N'-dioleyldipamide and N,N'-dierucylamide. The process is described in Patents EP 192 515 and EP 303 530.

Mention may be made of the copolyamides resulting from the condensation of at least two α,ω-aminocarboxylic acids or of two lactams or of one lactam and one α,ω-aminocarboxylic acid. As examples of alpha,omega-aminocarboxylic acid, mention may be made of aminocaproïc acid, 7-aminoheptanoïc acid, 11-aminoundecanoic acid, and 12-aminododecanoïc acid. Mention may also be made of copolyamides resulting from the condensation of at least one α,ω-aminocarboxylic acid (or a lactam), at least one diamine and at least one dicarboxylic acid. Mention may also be made of copolyamides resulting from the condensation of an aliphatic diamine with an aliphatic dicarboxylic acid and at least one other monomer chosen from aliphatic diamines that are different from the preceding one and aliphatic diacids that are different from the preceding one.

As examples of copolyamides, mention may be made of copolymers of caprolactam and lauryl lactam (PA-6/12), copolymers of caprolactam, adipic acid and hexamethylenediamine (PA-6/6,6), copolymers of caprolactam, lauryl lactam, adipic acid and hexamethylenediamine (PA-6/12/6,6), copolymers of caprolactam, lauryl lactam, 11-aminoundecanoic acid, azelaic acid and hexamethylenediamine (PA-6/6,9/11/12), copolymers of caprolactam, lauryl lactam, 11-aminoundecanoic acid, adipic acid and hexamethylenediamine (PA-6/6,6/11/12), copolymers of lauryl lactam, azelaic acid and hexamethylenediamine (PA-6,9/12), copolymers of 2-pyrrolidone and caprolactam (PA-4/6), copolymers of 2-pyrrolidone and lauryl lactam (PA-4/12), copolymers of caprolactam and 11-aminoundecanoic acid (PA-6/11), copolymers of lauryl lactam and of capryl lactam (PA-12/8), copolymers of 2-pyrrolidone and 11-aminoundecanoic acid (PA-11/4), copolymers of caprolactam and capryl lactam (PA-8/6), copolymers of 2-pyrrolidone and capryl lactam (PA-8/4) and copolymers of lauryl lactam and capryl lactam (PA-12/8).

It is possible to use polyamide and/or copolyamide blends. These are, for example, blends of aliphatic polyamides and of semi-aromatic polyamides and blends of aliphatic polyamides and of cycloaliphatic polyamides.

The powders may be manufactured by any means, dissolving in and precipitation from an alcohol. Advantageously, the powders are produced by polymerization in a solvent, the powders being insoluble in this solvent (anionic type polymerization defined above). Mention may be made of the process described in EP192 515 and EP303 530.

It is also possible to use copolyester amide powders resulting from the condensation of (the total being 100%):
1 to 98 mol % of a lactam;
1 to 98 mol % of a lactone; and optionally
1 to 98 mol % of another lactam different from the previous one.

The lactams that can be used to manufacture the copolyester amides are the same as those mentioned above. Advantageously, caprolactam and lauryl lactam are used. As examples of lactones, mention may be made of caprolactone, valerolactone and butyrolactone. Advantageously, caprolactone is used.

In the case of a copolyesteramide, the caprolactam, lauryl lactam and caprolactone are advantageously used in the following respective proportions (mol %): 30-46%, 30-46% and 8-40% (the total being 100%).

The process for preparing these copolyesteramide powders by anionic polymerization is described in the document EP 1 172 396.

Fatty Phase

A fatty phase may contain a liquid fatty phase and optionally a solid fatty phase (such as waxes). The liquid fatty phase may contain one or more oils that are liquid at room temperature (25° C.), these oils are volatile or non-volatile. The liquid fatty phase is formed from hydrocarbon-based oils or even optionally silicone oils.

The fatty phase comprises one or more oils, that is to say fatty substances that are immiscible with water. These volatile or non-volatile oils are of mineral, animal, plant or synthetic origin and may be hydrocarbon-based, silicone-based or fluorinated oils. The term "hydrocarbon-based oil" is understood to mean an oil essentially formed, or even composed of, carbon and hydrogen atoms and optionally oxygen or nitrogen atoms. It may contain alcohol, ester, ether, carboxylic acid, amine and/or amide groups.

It may contain one or more oils that are liquid at room temperature (25° C.), preferably at least one non-volatile liquid oil. The term "non-volatile liquid oil" is understood to mean an oil that is capable of remaining on the skin at room temperature (25° C.) and atmospheric pressure for at least one hour and that has, in particular, a non-zero vapour pressure at room temperature (25° C.) and atmospheric pressure which is less than or equal to 0.01 mmHg (1.33 Pa).

The liquid fatty phase advantageously comprises one or more non-volatile oils that provide an emollient effect on the skin. Mention may be made of fatty esters such as cetearyl isononoate, isotridecyl isononoate, isostearyl isostearate, isopropyl isostearate, isopropyl myristate, isopropyl palmitate, butyl stearate, hexyl laurate, isononyl isononoate, 2-ethylhexyl palmitate, 2-hexyldecyl laurate, 2-octyldecyl palmitate, 2-octyldodecyl myristate or lactate, di(2-ethylhexyl) succinate, diisostearyl malate, glyceryl or triglyceryl triisostearate, tocopherol acetate, higher fatty acids, such as myristic acid, palmitic acid, stearic acid, behenic acid, oleic acid, linoleic acid, linolenic acid or isostearic acid, caprylic/capric acid triglyceride, higher fatty alcohols, such as oleyl alcohol, avocado oil, camellia oil, macadamia nut oil, turtle oil, mink oil, soybean oil, grapeseed oil, sesame oil, maize oil, rapeseed oil, sunflower oil, cottonseed oil, jojoba oil, peanut oil, olive oil, hexyl laurate and mixtures thereof.

They may be mineral oils, hydrocarbon-based oils such as liquid paraffin, squalane, petroleum jelly and mixtures thereof.

Optionally, the composition comprises non-volatile silicone oils such as, for example, dimethylsiloxanes.

The liquid fatty phase may also optionally comprise volatile oils. The term "volatile oil" is understood to mean an oil capable of evaporating from the skin, in less than one hour at room temperature and atmospheric pressure. This oil has, in particular, a vapour pressure, at room temperature (25° C.) and atmospheric pressure (760 mmHg) that is greater than 0.01 and less than or equal to 300 mmHg (1.33 Pa to 40 000 Pa) and preferably ranging from 0.05 to 300 mmHg (6.65 Pa to 40 000 Pa).

The volatile oils are, for example, chosen from silicone oils that contribute to reducing the greasy effect of the formulations having a continuous fatty phase. Mention may be made of linear or cyclic silicone oils having a viscosity at room temperature less than 8 mm²/s and especially having from 2 to 7 silicon atoms, these silicones optionally comprising alkyl or alkoxy groups having from 1 to 10 carbon atoms. As a volatile silicone oil that can be used in the invention, mention may be made, in particular, of octamethylcyclotetrasiloxane, decamethylcyclopentasiloxane, dodecamethyl-cyclohexasiloxane, heptamethylhexyltrisiloxane, heptamethyloctyltrisiloxane, hexamethyldisiloxane, octamethyltrisiloxane, decamethyltetrasiloxane, dodecamethylpentasiloxane and mixtures thereof.

They are more particularly from the family of polyalkylsiloxanes or polyarylsiloxanes: cyclomethicone (DC 345 from Dow Corning), caprylylmethicone, cyclopentasiloxane (DC245 from Dow Corning).

Mention may also be made of the volatile hydrocarbon-based oils having from 8 to 16 carbon atoms and mixtures thereof, especially branched $C_8$ to $C_{16}$ alkanes, such as $C_8$ to $C_{16}$ isoalkanes (also known as isoparaffins), isododecane, isodecane, isohexadecane, branched $C_8$ to $C_{16}$ esters, such as isohexyl neopentanoate, and mixtures thereof.

Aqueous Phase

The aqueous phase contains water. The latter may be a floral water such as cornflower water and/or a mineral water, such as water from Vittel, water from Lucas or water from La Roche Posay and/or a thermal water. The aqueous phase may also comprise water-miscible constituents such as, for example, primary alcohols such as ethanol and isopropanol, polyols such as the glycols added for their humectant properties: glycerol, propylene glycol, butylene glycol, dipropylene glycol, diethylene glycol, glycol ethers such as mono-, di- or tripropylene glycol or mono-, di- or triethylene glycol (C1-C4) alkyl ethers, and mixtures thereof.

The aqueous phase may comprise, in addition, stabilizers such as sodium chloride, magnesium dichloride and magnesium sulphate.

The aqueous phase may also comprise any water-soluble or water-dispersible compound that is compatible with an aqueous phase, such as gelling agents, film-forming polymers, thickeners, surfactants and mixtures thereof.

Other Compounds

The cosmetic composition according to the invention may also comprise anionic, non-ionic or amphoteric type surfactants (generally lipophilic) facilitating the dispersion of the fatty phase in the aqueous phase so as to obtain a stable oil/water emulsion, additives such as preservatives (generally hydrophilic), fragrances (generally lipophilic), fillers different from the powder according to the invention, colouring materials (soluble dyes, pigments), thickeners (waxes, gelling agents), emulsion stabilizers (generally hydrophilic) or chelating agents (generally hydrophilic).

The surfactants may be of ester type such as sorbitan derivatives (e.g. sorbitan sesquiisostearate) or methyl glucose isostearate. They may be of polymer type, such as PEG-45/dodecyl glycol copolymer. They may also be silicone surfactants suitable for emulsifying silicone oils: they are for example dimethicone copolyols such as PEG/PPG-18/18 dimethicone, sold by Dow Corning under the name DC5225C.

The thickeners may be, for example, soluble in the fatty phase in order to adjust its consistency or to contribute to the stability of the composition: mention may be made, for example, of candelilla wax, silicone gums or elastomers (DC1411 and DC9040 from Dow Corning).

The preservatives are mixtures of paraben derivatives and/or phenoxyethanol.

Mention may be made, for example, of ethylenediaminetetraacetic acid (EDTA) as chelating agent.

It may also comprise cosmetic active agents that improve the aforementioned human keratinous substances. The cosmetic active agents comprise moisturizers (generally hydrophilic) such as polyols, UV radiation blockers, such as organic screening agents (generally lipophilic) or mineral particles, such as $TiO_2$ or ZnO which may or may not be surface-treated, antiwrinkle agents (generally hydrophilic), self-tanning agents (generally hydrophilic), film-forming agents (lipophilic or hydrophilic depending on their nature) or antioxidants (lipophilic or hydrophilic depending on their nature).

Mention may be made, as mineral screening agents, of dispersions of ZnO and of $TiO_2$ in mixtures of silicone oils.

For its part, the aqueous phase preferably comprises from 1 to 99 wt %, preferably from 10 to 60 wt %, of polyols relative to the total aqueous phase.

Furthermore, it may comprise 0.5 to 10%, preferably 3 to 5%, of surfactants, 0.01 to 2% of additives and 0.005 to 10% of cosmetic active agents relative to the total composition.

The characteristics of the coPA powders of the composition which is one subject of the invention are:
  the average diameter of the particles is from 0.1 to 100 µm, preferably from 0.5 to 50 µm, even more advantageously from 1 to 20 µm.
  the narrow particle size distribution. The particle size distribution of the powders is determined according to the usual techniques, for example using a Coulter Multisizer II particle size analyser, according to standard ISO 13319. From the particle size distribution it is possible to determine the average diameter and also the particle size dispersion (standard deviation), which measures the narrowing of the distribution. One of the advantages of the process described is that of making it possible to obtain a narrow distribution with a standard deviation between 1 and 3 µm, or even often less than 2 µm; and
  the advantageously spheroidal shape of the particles, that is to say in the form of a spheroid, which means: an approximately spherical solid.

The characteristics listed above contribute strongly to the soft feel in the systems having a continuous aqueous phase and to obtaining, after application, a matte and powdered appearance of the composition.

These characteristics also give the powders that are the subject of the invention the property of decreasing the appearance of wrinkles or of defects in the surface of the skin.

The examples in TABLES 1 to 4 below are defined in the following way:
Powder 1: Orgasol®2002EXD NAT COS, that is to say PA-12 powder, average diameter of the particles=10 µm, SSA=4±1.5 $m^2/g$, linseed oil uptake of 79 g/100 g, obtained according to the process described in EP192515.

Powder 2: Copolyamide PA-12/PA-6 (80/20) powder seeded ORGASOL®, particle size=10 µm, SSA=9.5±1 $m^2/g$,
Introduced into a reactor kept under nitrogen were: 2800 ml of solvent, then successively 108 g of caprolactam, 679 g of dry lauryl lactam, 14.4 g of EBS, and 112 g of finely divided ORGASOL® 2001 UD NAT1. After having started the stirring at 300 rpm, the mixture was gradually heated to 110° C., then 290 ml of solvent were distilled under vacuum in order to drive off, by azeotropy, traces of water which could be present.

After returning to atmospheric pressure, the anionic catalyst and 7.2 g of sodium hydride at 60% purity in oil were then rapidly introduced under nitrogen and the stirring was increased to 720 rpm, under nitrogen at 110° C. for 30 minutes.

Next, the temperature was brought down to 96° C. and, thanks to a small metering pump, a continuous injection, into the reaction medium, of the chosen activator, namely stearyl isocyanate (32.9 g made up to 314 g with solvent) was carried out according to the following programme:
  10 g/h of isocyanate solution over 300 minutes; and
  88 g/h of isocyanate solution over 180 minutes;

At the same time, the temperature was held at 96° C. for the first 360 minutes, then raised to 110° C. for 60 minutes and held at 110° C. for a further 2 hours after the isocyanate had finished being introduced.

The polymerization was then terminated, the reactor was almost clean. After cooling to 80° C., decanting and drying, the particle size was between 2 and 20 µm with the average diameter of the particles being 11.8 µm and the SSA was 9.3 $m^2/g$ without agglomerates.

Powder 3: Orgasol®3502 D NAT1 copolyamide PA-12/PA-6 (50/50) powder, average diameter of the particles=20 µm and SSA=2.5±1 $m^2/g$.

Powder 4: Copolyamide PA-12/PA-6 (50/50) powder, average diameter of the particles=10 µm, SSA=20±1 $m^2/g$, obtained according to the process described in EP192 515.

Powder 5: Orgasol®3202D NAT1 copolyamide PA-12/PA-6 (20/80) powder, average diameter of the particles=20 µm and SSA=1±1 $m^2/g$.

Powder 6: Orgasol®1002 D NAT COS, polyamide PA-6 powder, average diameter of the particles=20 µm and SSA=1±1 $m^2/g$.

The CONTROL composition does not comprise powder.

The percentages below are expressed by weight relative to the total composition. The nature of the compositions comprising powders 1 to 6 is defined below for each table.

The effect of adding PA powders according to the invention into emulsions having a continuous aqueous phase was measured by sensory analysis in various types of compositions. Each composition was the subject of a sensory profile study, conducted by a panel of five experts according to the following specifications:
  during the phase of application of the product: the richness, the speed of penetration; and
  immediately after application: the shininess of the skin, the softness of the skin, the powder residue left by the composition on the skin.

Each composition was analysed under blind conditions by comparison of all the tests forming a series.

The results are collated in TABLES 1 to 4. The various criteria were evaluated on a scale ranging from 0 to 8. The value 0 indicating the absence of the designated criteria (for example, a feeling of absence of softness); the value 8 indicating a very marked tendency for the chosen criteria (for example, a very great feeling of presence of softness).)

Compositions A to F and Control 1 are compositions of oil-in-water emulsion type, comprising 5% of fatty phase corresponding, for example, to light cream compositions.

The process for preparing the compositions below consisting in (1) combining and heating the aqueous phase A to 75° C., (2) combining and heating the fatty phase (B) to 75° C., (3) slowly adding the fatty phase B to the phase A while vigorously stirring so as to form an emulsion, then (4) cooling to room temperature before adding the constituents of the phase C with stirring and then the powder (phase D) (except for the control) while gently stirring.

| | Ingredients (INCI names) | wt % |
|---|---|---|
| A | Water | q.s. for 100 |
| | Carbomer | 0.40 |
| | Sodium hydroxide (10% in water) | 0.10 |
| | Glycerol | 3.00 |
| | Phenoxyethanol, methylparaben, ethylparaben, butylparaben, propylparaben, isobutylparaben | 0.60 |
| | Chlorophenesin | 0.25 |
| B | PEG-100 Stearate, Glyceryl Stearate | 1.50 |
| | Myristyl Alcohol, Myristyl Glucoside | 1.00 |
| | Hexyl Laurate | 5.00 |
| C | Sodium PCA | 0.20 |
| | Polyacrylamide, C13-14 Isoparaffin, Laureth-7 | 1.00 |
| | sodium hydroxide (10% in water) | 0.60 |
| D | Powder 1 to 6 according to composition A to F | 3.50 |

Control 1: x = 0% of powder.
Composition A: x = 3.5% of powder 1.
Composition B: x = 3.5% of powder 2.
Composition C: x = 3.5% of powder 3.
Composition D: x = 3.5% of powder 4.
Composition E: x = 3.5% of powder 5.
Composition F: x = 3.5% of powder 6.

TABLE 1

| | | Control 1 | A | B | C | D | E | F |
|---|---|---|---|---|---|---|---|---|
| Behaviour during application | Richness | 2 | 2.5 | 5 | 4.5 | 5 | 6 | 4 |
| | Speed of penetration | 2.5 | 4 | 4 | 6 | 5.5 | 4 | 4 |
| Behaviour after application | Shininess | 2 | 0.5 | 2 | 2 | 2 | 2 | 2 |
| | Softness | 2 | 5 | 6 | 3.5 | 4.5 | 3.5 | 3.5 |
| | Powder residue | 0 | 5 | 6.5 | 3 | 4 | 2 | 2 |

Compositions G to L and Control 2 in TABLE 2 are compositions of oil-in-water emulsion type comprising 10% of fatty phase which may correspond, for example, to moisturizing day creams, known as rich creams.

The process for preparing the compositions below consisted in (1) combining and heating the aqueous phase A to 75° C., (2) combining and heating the fatty phase B to 75° C., (3) slowly adding the fatty phase B to the phase A while vigorously stirring so as to form an emulsion and then (4) cooling to room temperature before adding the constituents of the phase C with stirring and then the powder (phase D) (except for the contrail while gently stirring.

| | Ingredients (INCI names) | wt % |
|---|---|---|
| A | Water | q.s. for 100 |
| | Glycerol | 3.00 |
| | Phenoxyethanol, methylparaben, ethylparaben, butylparaben, propylparaben, isobutylparaben | 0.60 |
| | Chlorophenesin | 0.20 |
| B | Cetearyl Alcohol, Cetearyl Glucoside | 6.00 |
| | Caprylic/Capric Triglyceride | 5.00 |
| | Squalane | 3.00 |
| | Dimethicone | 1.00 |
| | Shea butter | 1.00 |
| | Cetearyl alcohol | 1.00 |
| | Cetyl Acetate, Acetylated Lanolin Alcohol | 0.50 |
| C | PEG-8, Tocopherol, Ascorbyl Palmitate, Ascorbic Acid, Citric Acid | 0.10 |
| | Polyacrylamide, C13-14 Isoparaffin, Laureth-7 | 0.40 |
| | Sodium hydroxide (10% in water) | 0.01 |
| D | Powder 1 to 6 according to composition G to L | 3.50 |

Control 2: x = 0% of powder.
Composition G: x = 3.5% of powder 1.
Composition H: x = 3.5% of powder 2.
Composition I: x = 3.5% of powder 3.
Composition J: x = 3.5% of powder 4.
Composition K: x = 3.5% of powder 5.
Composition L: x = 3.5% of powder 6.

TABLE 2

| | | Control 2 | G | H | I | J | K | L |
|---|---|---|---|---|---|---|---|---|
| Behaviour during application | Richness | 2.5 | 3 | 4 | 5 | 5 | 2 | 6 |
| | Speed of penetration | 2.5 | 4 | 5 | 6 | 5.5 | 5 | 5.4 |
| Behaviour after application | Shininess | 2.5 | 1.5 | 0.5 | 2.5 | 2.5 | 2.5 | 2.5 |
| | Softness | 2 | 4.5 | 7 | 5 | 6 | 2 | 3.5 |
| | Powder residue | 0 | 4 | 7 | 5 | 4 | 3 | 2 |

The addition of 0.2 wt % to 30 wt %, preferably from 0.5 wt % to 10 wt %, of coPA powders into an oil-in-water emulsion (day cream, moisturizing fluid, body milk or aftershave care type, amongst others) makes it possible to provide richness to the formulations, which is linked to the consistency. Furthermore, after application, the use of this copolyamide powder makes it possible to give the skin a soft feel, which is much greater than that obtained for pure PA powders. Finally, after application, the formulations leave a powder residue on the skin which scatters the light and masks imperfections. The addition of powder makes it possible to obtain a matte, smooth, natural and powdered appearance.

In particular, in a composition of Control 1 type containing a small amount of fatty phase, the addition of coPA powder significantly increases the consistency of the cream and enables it to give an impression of richness to the user, without increasing the oily compounds which could lead to a greasy feeling. After application, the coPA powders containing more than 20 mol % of PA-12 give a softer feel and a more noticeable powder residue.

In particular, in a composition of Control 2 type containing a larger amount of fatty phase, the addition of coPA powder significantly increases the consistency of the cream and enables it to give an impression of richness to the user, without increasing the oily compounds which could lead to a greasy feeling. After application, the coPA powders containing more than 50% of PA-12 give a softer feel, a more noticeable powder residue and a greater smoothing effect.)

Compositions M to N and Control 3 in TABLE 3 are compositions of oil-in-water emulsion type comprising 15.5% of fatty phase. These compositions correspond, for example, to the formulations of antiwrinkle creams.

| Ingredients (INCI names) | | wt % |
|---|---|---|
| A | Water | q.s. for 100 |
| | Acrylates/C10-30 Alkyl Acrylate Crosspolymer | 0.2 |
| | Glycerol | 2.0 |
| | Chlorophenesin | 0.2 |
| | Phenoxyethanol, methylparaben, ethylparaben, butylparaben, propylparaben, isobutylparaben | 0.6 |
| B | Stearic Acid | 12.0 |
| | Polysorbate 80 | 0.6 |
| | *Butyrospermum Parkii* (Shea Butter) | 1.0 |
| | Caprylic/Capric triglyceride | 7.0 |
| | Squalane | 3.5 |
| | PPG-15 Stearyl Ether, BHT | 1.0 |
| C | Triethanolamine | 0.556 |
| D | Cyclopentasiloxane, Cyclohexasiloxane | 3.0 |
| E | PEG-8, Tocopherol, Ascorbyl Palmitate, Ascorbic Acid, Citric Acid | 0.07 |
| | Fragrance | 0.3 |
| F | Powder 1 to 2 according to composition M to N | x |

Control 3: x = 0% of powder.
Composition M: x = 3.5% of powder 1.
Composition N: x = 3.5% of powder 2.

The process for preparing the compositions below consisted in (1) combining and heating the aqueous phase A to 75° C., (2) combining and heating the fatty phase B to 75° C., (3) slowly adding the fatty phase B to the phase A while vigorously stirring so as to form an emulsion, then (4) adding C just after the emulsion (pH=6.9), then (5) cooling to 60° C. before adding D, then (6) cooling to room temperature before adding the constituents of the phase E, then (7) adding the powder (phase F) (except for the control) while gently stirring.

TABLE 3

| | | Control 3 | Composition M | Composition N |
|---|---|---|---|---|
| Behaviour during application | Richness | 2.5 | 1.5 | 3.5 |
| | Speed of penetration | 2 | 4 | 3.5 |
| Behaviour after application | Shininess | 2 | 0 | 0.5 |
| | Softness | 4 | 4.5 | 6.5 |
| | Powder residue | 0 | 4 | 5.5 |

In the formulations of oil-in-water emulsion type comprising 15.5% of fatty phase characterized in Table 3, the copolyamides provide a softness and a powder residue that are much superior to the pure polyamide PA-12 powders.

Furthermore, the smoothing effect of the composition N was measured by the fringe projection method, the principle of which is the following: measurement of the cutaneous relief by projection of fringes was carried out at a crows foot for 20 healthy female subjects.

The fringe projection technique makes it possible to document changes in the cutaneous topography of the crows foot. The measurements were carried out using an optical system dedicated to the metrology of the relief of surfaces.

This system comprises a sensor connected to a projector and to a high-resolution CCD camera. The average axial and lateral resolutions are of the order of 10 μm.

Analysis of the cutaneous surface topography was carried out by calculating the standard roughness parameters. These parameters were extracted from an area measuring 30×40 mm (12 cm$^2$), expressed in mm.

The parameters quantified were over a series of profiles perpendicular to the wrinkles and fine lines of the region of interest.

For example, the parameter SPt (maximum amplitude of the relief) was extracted. For the crows foot, the decrease in SPt signifies a reduction of the main wrinkle.

The formulation N resulted in a 4% reduction of the SPt parameter 20 minutes after applying the product to the crows foot zone and a 6% reduction after 2 hours.

This result corresponds to a significant decrease of the roughness parameter SPt (maximum amplitude of the relief) from 20 minutes after applying the product (−4% on average over the whole panel), confirmed and amplified 2 hours after application (−6% on average over the whole panel). This significant variation translates into a reduction, in depth, of the main wrinkle of the crows foot.)

Compositions O to P and Control 4 in TABLE 4 are compositions of oil-in-water emulsion type comprising 26.5% of fatty phase. These compositions correspond, for example, to sun cream formulations having a high protection factor.

For this type of formulation, an additional specification has been added to the sensory study, especially suitable for sunscreen formulations having a high protection factor: this is the white residue, observed after application, due to the sunscreening agents. This specification is evaluated to be 0 when after applying the formulation, no white residue remains on the skin; it is evaluated to be 8 when, after application, a large white residue remains on the skin.

The process for preparing the compositions below consisted in (1) combining and heating the aqueous phase A to 70° C., (2) combining and heating the fatty phase B to 70° C., (3) slowly adding the fatty phase B to the phase A while vigorously stirring so as to form an emulsion, then (4) cooling to room temperature before adding the constituents of the phase C, and then (5) of the phase D with stirring, and then (6) the powder (phase E) (except for the control) while gently stirring.

| Ingredients (INCI Name) | | wt % |
|---|---|---|
| A | Water | q.s. for 100 |
| | Ammonium Acryloyldimethyltaurate/VP Copolymer | 0.6 |
| | Phenoxyethanol, methylparaben, ethylparaben, butylparaben, propylparaben, isobutylparaben | 0.9 |
| | Chlorophenesin | 0.3 |
| | Butylparaben | 0.4 |
| B | Lauryl Glucoside, Polyglyceryl-2 Dipolyhydroxystearate, Glycerol, Aqua (water) | 9.0 |
| | Dicaprylyl carbonate | 7.0 |
| | C12-15 Alkyl Benzoate | 7.0 |
| | Ethylhexyl Methoxycinnamate | 7.5 |
| | Ethylhexyl Salicylate | 5.0 |
| | Butyl Methoxydibenzoylmethane | 2.0 |
| C | Tocopheryl Acetate | 0.1 |
| D | Methylene Bis-Benzotriazolyl Tetramethylbutylphenol, Aqua (water), Decyl Glucoside, Propylene Glycol, Xanthan Gum | 20.0 |
| | Citric Acid | 0.0256 |
| | Fragrance | 0.3 |
| E | Powder 1 to 2 according to composition O to P | x |

Control 4: x = 0% of powder.
Composition O: x = 5% of powder 1.
Composition P: x = 5% of powder 2.

TABLE 4

| | | Control 4 | Composition O | Composition P |
|---|---|---|---|---|
| Behaviour during application | Richness | 2.5 | 1 | 4 |
| | Speed of penetration | 3 | 2 | 4.5 |
| Behaviour after application | Shininess | 3.5 | 2 | 2 |
| | Softness | 0 | 3 | 6 |
| | Powder residue | 0 | 4 | 6 |
| | White residue | 4 | 4 | 1.5 |

In the formulations of oil-in-water emulsion type comprising 26.5% of fatty phase characterized in Table 4, the copolyamides provide a softness and a powder residue that are much superior to the pure polyamide PA-12 powders; they decrease the whitening effect of the sunscreening agents more substantially.

The invention claimed is:

1. A composition comprising in % by weight relative to total composition, (i) 59.9 to 98.9% of an aqueous phase, (ii) 40 to 1% of a fatty phase and (iii) 0.1 to 30% of a pulverulent phase comprising copolymers of caprolactam and lauryl lactam (PA-6/12), said composition being an oil-in-water emulsion.

2. The composition according to claim 1, wherein the pulverulent phase is particles of spheroidal shape having an average diameter ranging from 1 μm to 200 μm.

3. The composition according to claim 2, wherein the particles have a specific surface area between 1 and 25 $m^2/g$.

4. The composition according to claim 1, wherein the aqueous phase comprises from 1 to 99 wt % of polyols relative to the total aqueous phase.

5. The composition according to claim 1, comprising, in addition (% by weight relative to the total composition):
from 0.5 to 10% of surfactants;
from 0.01 to 2% of additives; and
from 0.005 to 10% of cosmetic active agents.

6. The composition according to claim 5, wherein the additives are preservatives, fragrances, fillers that are different from the pulverulent phase, coloring substances, thickeners, emulsion stabilizers, or chelating agents.

7. The composition according to claim 5, wherein the cosmetic active agents are moisturizers, UV screening agents, antiwrinkle agents, self-tanning agents, film-forming agents or antioxidants.

8. The composition according to claim 1, that is a moisturizing, antiwrinkle and/or make-up-removing face care cream or fluid, a moisturizing and/or slimming body care cream or fluid, a waterproof or non-waterproof sun cream, a foundation, an eye shadow, a mascara, a blusher, a concealer or a body makeup product, a two-phase moisturizing or make-up-removing lotion.

9. A process for manufacturing a make-up and/or care product for the skin which gives the skin a soft feel and a matt and powdered appearance after application onto said skin, comprising producing said make-up or care product by combining a composition according to claim 1 and a cosmetic active agent.

10. A process for making up and/or caring for keratinous substances, comprising application to these substances of a composition according to claim 1.

11. A composition comprising in % by weight relative to total composition, (i) 59.9 to 98.9% of an aqueous phase, (ii) 40 to 1% of a fatty phase and (iii) 0.1 to 30% of a pulverulent phase comprising copolymers of caprolactam and lauryl lactam (PA-6/12), said composition being an oil-in-water emulsion, and wherein the pulverulent phase is particles of spheroidal shape having an average diameter of 1-200 μm, a specific surface area of 1-25 $m^2/g$, said aqueous phase comprises 1-99% by weight of polyols relative to total aqueous phase, and, by weight relative to the total composition, (iv)

0.5 to 10% of surfactants;

0.01 to 2% of preservatives, fragrances, fillers different from the pulverulent phase, coloring substances, thickeners, emulsion stabilizers or chelating agents, 0.005 to 10% of moisturizers, UV screening agents, anti-wrinkle agents, self-tanning agents, film-forming agents or antioxidants.

* * * * *